United States Patent
Kotani

(10) Patent No.: US 6,782,323 B2
(45) Date of Patent: Aug. 24, 2004

(54) METHOD AND PROGRAM FOR EVALUATING MOLECULAR SIMILARITY

(75) Inventor: Takayuki Kotani, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 134 days.

(21) Appl. No.: 10/133,539

(22) Filed: Apr. 25, 2002

(65) Prior Publication Data

US 2003/0023391 A1 Jan. 30, 2003

(30) Foreign Application Priority Data

Apr. 26, 2001 (JP) .................................. 2001-129216

(51) Int. Cl.[7] .............................................. G01N 31/00
(52) U.S. Cl. ........................ 702/27; 702/19; 702/27; 702/30; 702/179; 356/939; 356/925; 703/2; 703/11; 703/12; 250/251; 250/281; 250/306
(58) Field of Search ...................... 702/19, 21, 30–32, 702/158–159, 179, 181, FOR 115–119, FOR 131, FOR 134, FOR 139, FOR 140, FOR 146, FOR 170; 356/939, 925; 703/2, 12, 11; 250/251, 281, 306

(56) References Cited

U.S. PATENT DOCUMENTS 5,526,281 A * 6/1996 Chapman et al. ........... 364/496

2003/0049687 A1 * 3/2003 Skolnick ...................... 435/7.1

OTHER PUBLICATIONS

Popelier, "A Fast and Reliable Molecular Similarity Index Based on Electron Density", Dec. 2000, UMIST, pp. 1–8.*

Blinn et al., "Field–Based Similarity Forcing in Energy Minimization and Molecular Matching", Dec. 1999, Pharmacia & Upjohn, pp. 1–11.*

Podlipnik et al., "A Comparative Study of Electrostatic Similarity Indices", Feb. 1998, University of Ljubljana, pp. 689–696.*

* cited by examiner

Primary Examiner—Marc S. Hoff
Assistant Examiner—Elias Desta
(74) Attorney, Agent, or Firm—Harness, Dickey & Pierce, PLC

(57) ABSTRACT

A molecular similarity evaluation method has steps of: (a) obtaining an upper threshold and a lower threshold from one of a value specific to an atom included in a first molecule, a value specific to an atom included in a second molecule of which correlation with respect to the atom in the first molecule is to be evaluated, or another value obtained from these values; (b) calculating the correlation between the atom in the first molecule and the atom in the second molecule, using the upper and lower thresholds; and (c) evaluating the similarity between the first and second molecules based on the correlation obtained in the step (b).

22 Claims, 5 Drawing Sheets

METHOD AND PROGRAM FOR EVALUATING MOLECULAR SIMILARITY

FIELD OF THE INVENTION

The present invention relates to a method and program of evaluating shape similarity between two molecules.

BACKGROUND OF THE INVENTION

Used as methods of designing drug molecules having desired physiological activity are logical molecular design techniques using the three-dimensional quantitative structure-activity relationships (3D-QSAR) analysis and pharmacophore mapping. In these methods, existing drugs are superimposed on each other in a three-dimensional virtual space according to appropriate rules, and statistical processing is performed on the superimposed drugs using the partial least square of latent valuables (PLS) method, neural net (NN) method, genetic algorithm (GA), or the like. Thus, features between the activity and various parameters of the drugs are extracted. The graphical display of the obtained results allows visual recognition of the parts contributing to the activity in the molecular structure (e.g. a functional group and stereo-structure) and gives a cue of molecular design. These methods are also applied to forecasting the activity of a newly designed molecule.

Techniques for superimposing molecules are important in the 3D-QSAR and the pharmacophore search. Conventionally used are the methods of: improving the degree of superimposition by gradually moving a plurality of molecules to be compared so that the root mean square of atoms or functional groups corresponding to one another is minimum; and sequentially searching the best superimposition using an evaluation function (molecular similarity).

However, in the method of superimposing the atoms or functional groups, a researcher's subjective view is inevitable, although the superimposing operation is performed within a short period of time. The method of automatically extracting the functional groups using a computer poses a problem: the method of selecting the types and the number of functional groups to be superimposed include software-dependant arbitrariness and a researcher's subjective view. On the other hand, the method using an evaluation function poses another problem of requiring prolonged calculation time, although it is ideal as a technique of superimposing molecules.

For example, a molecular similarity evaluation method, proposed by Carbo et al., of comparing the electron densities of molecules, requires prolonged calculation time. For this reason, another molecular similarity evaluation method using comparison of the molecular electrostatic potential (MEP) or molecular shape is proposed.

In a molecular shape similarity evaluation method that has been proposed by Meyer et al. and disclosed in the Journal of Computer-Aided Molecular Design, 5(1991), 427–439, "Similarity of Molecular Shape", molecular similarity is evaluated using the following equation:

$$S_{AB} = \frac{C}{(T_A \cdot T_B)^{1/2}}$$

where $T_A$ and $T_B$ represent the volumes of two molecules A and B, respectively, and C represents the area of a part common to molecules A and B when they are superimposed on each other. When molecules A and B are completely superimposed on each other, a maximum value of +1 is given to $S_{AB}$. When molecules A and B have no common part, 0 is given to $S_{AB}$. The value of each volume is calculated by counting grid points that fall inside of each molecule or the van der Waals radii of both molecules, among the grid points generated at regular intervals.

However, the molecular similarity evaluation using grid points requires prolonged calculation time. Extremely fine grids (typically 0.2 Å separation) are required to obtain accurate results. Therefore, a high-speed computer, such as a workstation, is required to obtain an optimum model of superimposed molecules.

In order to address this problem, Richards et al. have calculated the Gaussian function using the distance between an atom in a template molecule and an atom in a molecule to be compared to apply the function to the calculation of molecule similarity. Refer to the Perspectives in Drug Discovery and Design, 9/10/11: 321–338, 1998, "Explicit Calculation of 3D Molecular Similarity". This method can attain molecular similarity evaluation considerably faster than the method by Meyer et al. However, in the calculation of molecular similarity, the atomic distance between every atom in a molecule and every atom in the other molecule must be calculated. Therefore, the calculation still requires considerable time.

As mentioned above, the conventional molecular similarity evaluation methods require prolonged calculation time. Therefore, it has been difficult to repeatedly obtain molecule similarity, and obtain an optimum superimposition model based on the results, using such methods as the simplex optimization. The method of superimposing molecules so that one functional group is within a constant distance from the other functional group is effective especially when the pharmacophore is already clear. However, this method does not provide any excellent superimposition model of small molecules having a small number of functional groups.

The present invention, therefore, provides a method of easily evaluating molecular similarity at a high speed, and a method of obtaining an optimum superimposition model by moving molecules so as to maximize the similarity, and moreover, a program of executing these methods.

SUMMARY OF THE INVENTION

In order to address the problems discussed above, the present invention provides a molecular similarity evaluation method of evaluating the similarity between a first molecule and a second molecule, comprising the steps of:

(a) obtaining an upper threshold and a lower threshold from one of a value specific to an atom included in the first molecule, a value specific to an atom included in the second molecule of which correlation with respect to the atom in the first molecule is to be evaluated, or another value obtained from these values;

(b) calculating the correlation between the atom in the first molecule and the atom in the second molecule, using the upper and lower thresholds; and (c) evaluating the similarity between the first and second molecules based on the correlation obtained in the step (b).

In accordance with another aspect of the present invention, there is provided a molecular similarity evaluation method of obtaining the correlation between each atom included in a first molecule and each atom included in a second molecule based on the atomic distance therebetween and evaluating the similarity between the first and second molecules based on this correlation. The operation of obtaining the correlation between the atoms includes steps of:

(a) obtaining a value specific to an atom in the first molecule and/or an atom in the second molecule;

(b) obtaining an upper threshold from the specific value obtained in the step (a);

(c) obtaining a lower threshold from the specific value obtained in the step (a);

(d) obtaining a distance between the two atoms; and (e) evaluating the correlation between the atom in the first molecule and the atom in the second molecule, using the atomic distance obtained in the step (d), the upper threshold, and the lower threshold.

In accordance with further aspect of the present invention, there is provided a method and program of evaluating similarity between a first molecule and a second molecule disposed in a three-dimensional coordinate system, comprising steps of:

(a) resetting a correlation coefficient;

(b) selecting one atom from a plurality of atoms included in the second molecule;

(c) selecting one atom from a plurality of atoms included in the first molecule;

(d) obtaining an upper threshold and a lower threshold from a value specific to both or one of the atoms selected in each of the steps (b) and (c);

(e) obtaining a distance between the atoms selected in each of the steps (b) and (c);

(f) obtaining a correlation coefficient based on the upper and lower thresholds obtained in the step (d), according to the atomic distance obtained in the step (e);

(g) determining whether or not any atom unselected from the plurality of atoms included in the first molecule exists, after completion of the step (f);

(h) when it is determined in the step (g) that any atom unselected from the plurality of atoms included in the first molecule exists, returning to the step (c), selecting another atom unselected from the plurality of atoms in the first molecule, executing the steps (d) through (f), and updating the correlation coefficient; and (i) when it is determined in the step (g) that any atom unselected from the plurality of atoms included in the first molecule does not exist, returning to step (a), selecting another atom unselected from the plurality of atoms in the second molecule, executing the steps (c) through (h), and adding the correlation coefficient.

Preferably, in the step (d), the relative position of the first and second molecules is changed in a direction to improve the similarity index.

In accordance with still further aspect of the present invention, there is provided a method and program of evaluating similarity of two molecules, including steps of:

(a) obtaining a three-dimensional coordinate of each atom included in first and second molecules;

(b) disposing the first and second molecules in a three-dimensional coordinate system;

(c) obtaining a similarity index of each atom included in the second molecule with respect to each atom included in the first molecule, comprising sub-steps of:

(c-0) resetting a correlation coefficient;

(c-1) selecting one atom from a plurality of atoms included in the second molecule;

(c-2) selecting one atom from a plurality of atoms included in the first molecule;

(c-3) obtaining an upper threshold and a lower threshold from values specific to both or one of the atoms selected in each of the sub-steps (c-1) and (c-2);

(c-4) obtaining a distance between the atoms selected in each of the sub-steps (c-1) and (c-2);

(c-5) obtaining a correlation coefficient according to the atomic distance obtained in the sub-step (c-4), based on the upper and lower thresholds obtained in the sub-step (c-3);

(c-6) determining whether or not any atom unselected from the plurality of atoms included in the first molecule exists, after completion of the sub-step (c-5);

(c-7) when it is determined in the sub-step (c-6) that any atom unselected from the plurality of atoms included in the first molecule exists, returning to the sub-step (c-2), selecting another atom unselected from the plurality of atoms in the first molecule, executing the sub-steps (c-3) through (c-6), and updating the correlation coefficient; and (c-8) when it is determined in the sub-step (c-6) that any atom unselected from the plurality of atoms included in the first molecule does not exist, returning to the sub-step (c-0), selecting another atom unselected from the plurality of atoms in the second molecule, executing the sub-steps (c-2) through (c-7), and adding the correlation coefficient so as to obtain the similarity index; and (d) changing the relative position of the first molecule and the second molecule in the three-dimensional coordinate system, after the completion of the step (c).

The atomic distance obtained in the above-mentioned plurality of aspects can be a distance with respect to one of axes in the Cartesian coordinate system.

For the value specific to an atom, one of the van der Waals radius, atomic radius, and covalent radius of the atom can be used.

Preferably, the upper threshold is obtained by multiplying a value specific to the atom by an upper limit constant, and the lower threshold is obtained by multiplying a value specific to the atom by a lower limit constant. Preferably, the upper limit constant is a value ranging from 1.0 to 1.3 and the lower limit constant is a value ranging from 0.5 to 0.8.

DETAILED DESCRIPTION OF THE EMBODIMENTS

Similarity evaluation of two molecules using a superimposition method will be described with reference to the accompanying drawings. The following process is performed by starting a program coded in accordance with the present invention on an appropriate computer. Of course, the computer includes various devices necessary to execute the program (e.g. CPU, and internal and external memories). The program can run on one of various operating systems available now. System configuration and applications running on the system do not limit the present invention. The program is recorded on various existing recording media, e.g. CD-ROM, or provided via the Internet or such communication lines as a telephone line.

Figure 1:
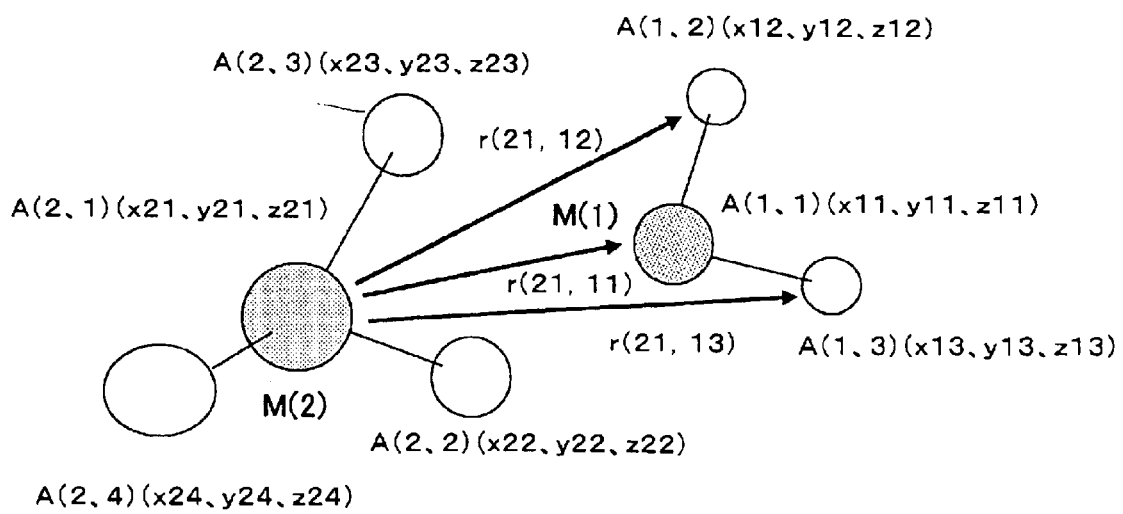
FIG. 1 is a drawing for illustrating a molecular similarity evaluation method in accordance with the present invention.
Figure 2:
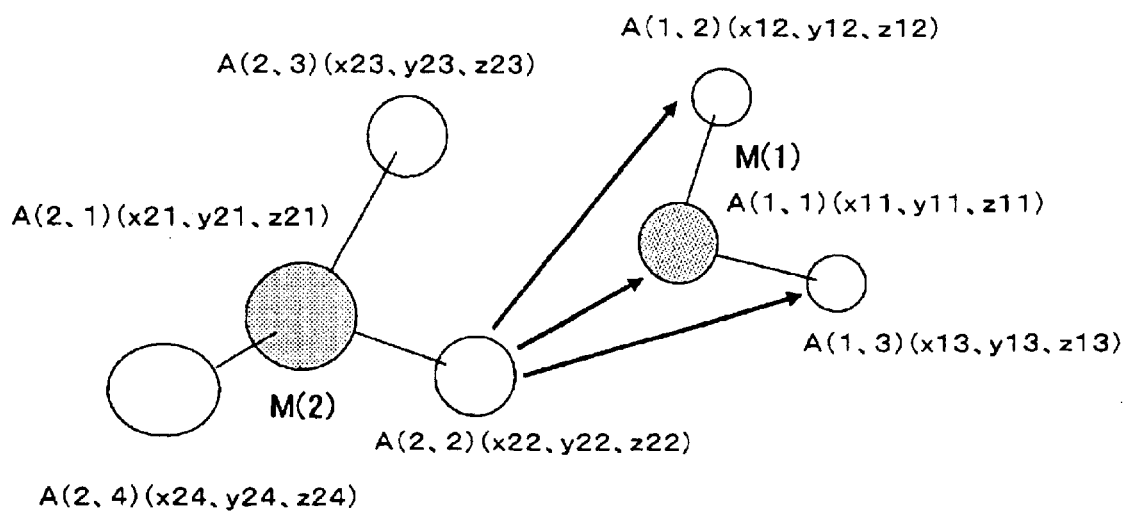
FIG. 2 shows molecular models used for illustrating the molecular similarity evaluation method in accordance with the present invention together with FIG. 1.
Figure 3:
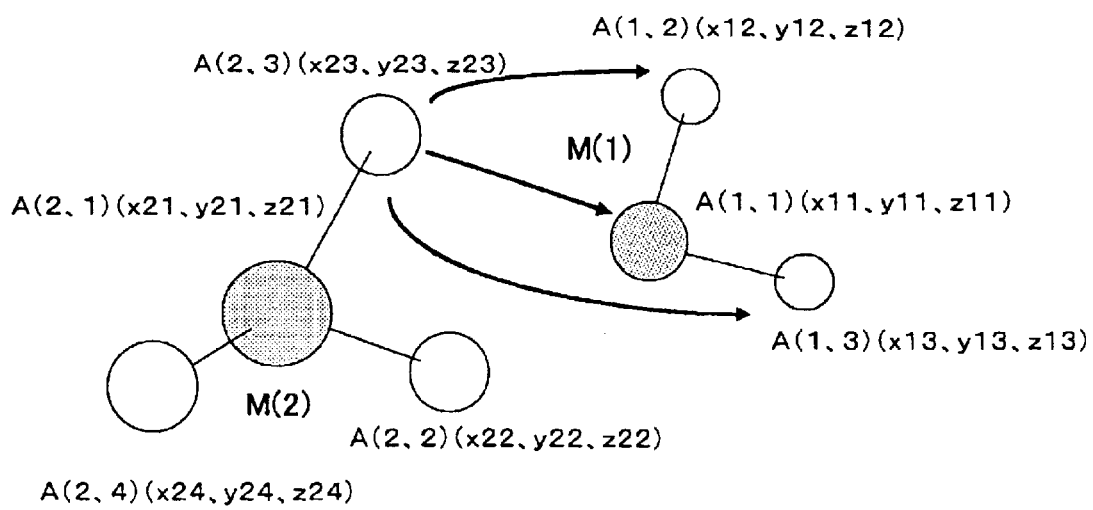
FIG. 3 shows molecular models used for illustrating the molecular similarity evaluation method in accordance with the present invention together with FIGS. 1 and 2.
Figure 4:
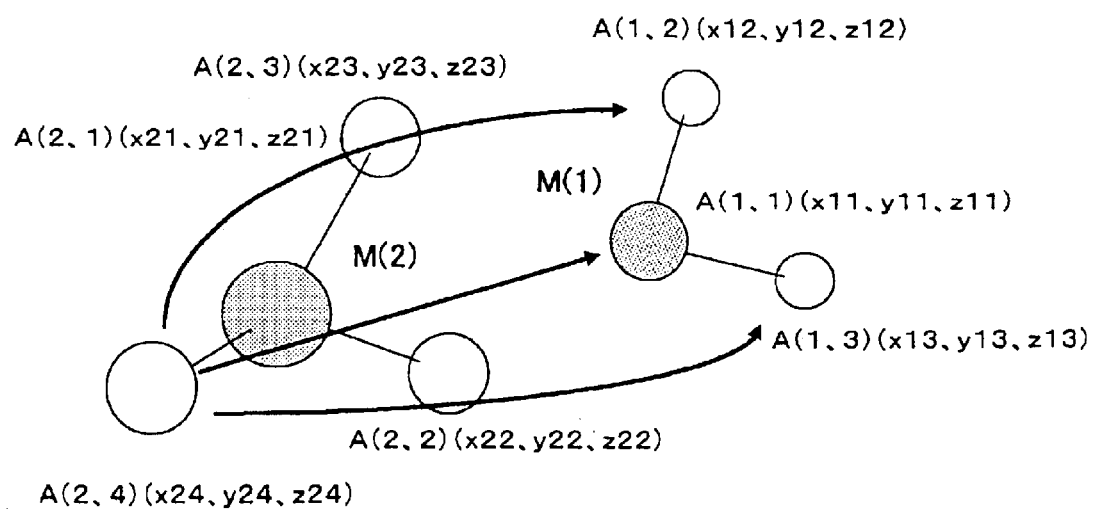
FIG. 4 shows molecular models used for illustrating the molecular similarity evaluation method in accordance with the present invention together with FIGS. 1 to 3.
Figure 5:
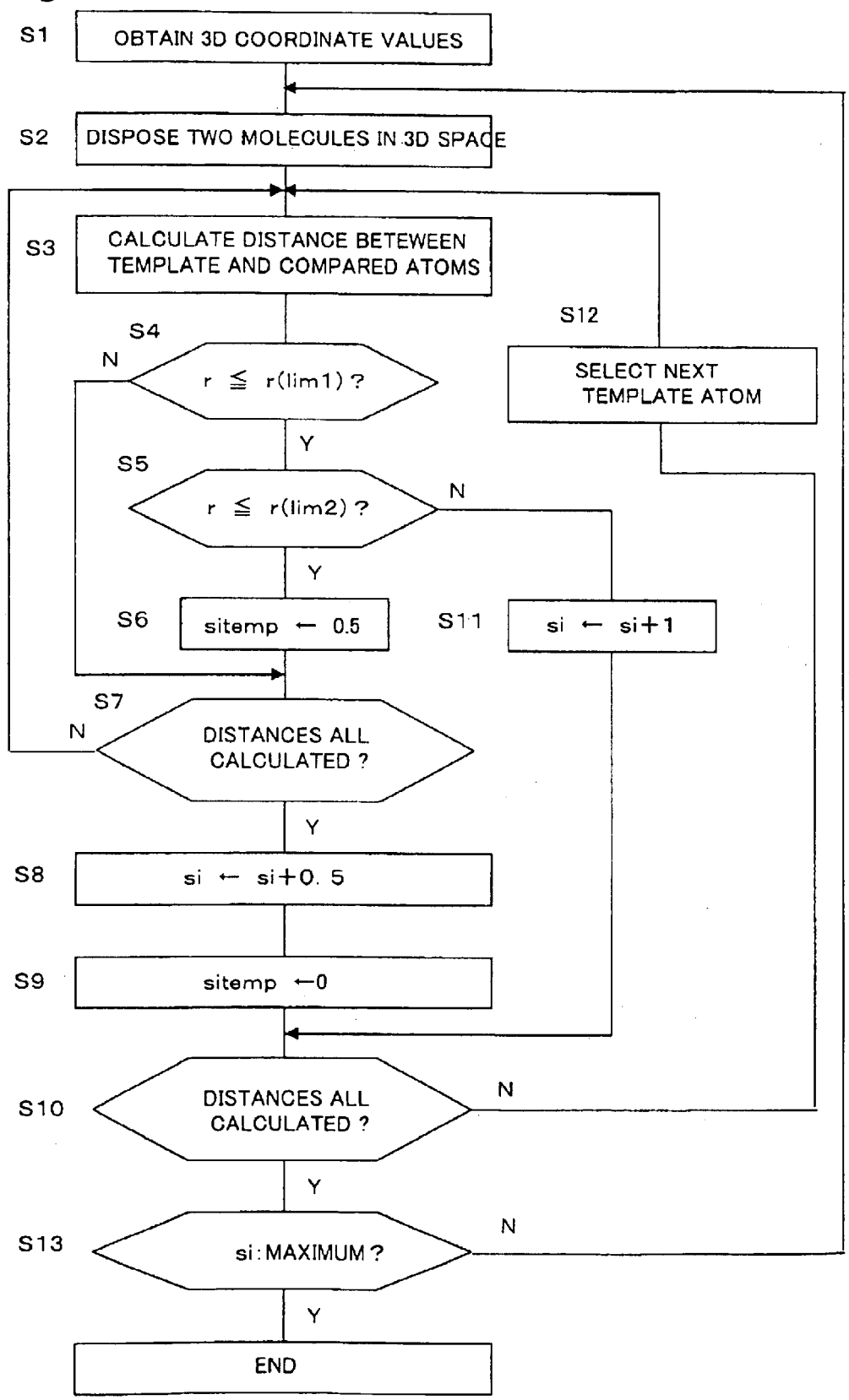
FIG. 5 is a schematic flowchart of the molecular similarity evaluation method and a program thereof in accordance with the present invention.

The similarity evaluation will be described, using first molecule M (1) and second molecule M (2) shown in FIGS. 1 to 4 as an example, with reference to the flowchart in FIG. 5. In the similarity evaluation method of the present invention, first, three-dimensional coordinate values (e.g. X, Y, and Z coordinates) of an atom included in each of the molecules M (1) and M (2) are obtained (Step 1). Next, the two molecules M (1) and M (2) are disposed in a three-dimensional virtual space (the Cartesian coordinate space), utilizing the obtained three-dimensional coordinate values (Step 2). Suppose that the first molecule M (1) comprises three atoms [A (1, 1), A (1, 2), A (1, 3)], the second molecule M (2) comprises four atoms [A (2, 1), A (2, 2), A (2, 3), A (2, 4)], and each atom in the two molecules M (1) and M (2) disposed in the three-dimensional coordinate space has the coordinates shown in the following Table 1.

TABLE 1

| Molecule | Atom | X coordinate | Y coordinate | Z coordinate |
|---|---|---|---|---|
| M (1) | A (1, 1) | x11 | y11 | z11 |
|  | A (1, 2) | x12 | y12 | z12 |
|  | A (1, 3) | x13 | y13 | z13 |
| M (2) | A (2, 1) | x21 | y21 | z21 |
|  | A (2, 2) | x22 | y22 | z22 |
|  | A (2, 3) | x23 | y23 | z23 |
|  | A (2, 4) | x24 | y24 | z24 |

In Step 3, the atomic distance of a selected atom in the second molecule M (2) from a selected atom in the first molecule M (1) is calculated. For convenience, the second molecule having a larger number of atoms is called a "template molecule", and the first molecule having a smaller number of atoms is called a "compared molecule". Atoms included in the template molecule are called "template atoms", and atoms included in the molecule to be compared are called "compared atoms", as required. In this embodiment, the second molecule M (2) is a template molecule and the first molecule M (1) is a compared molecule.

In the example shown, a distance r (21, 11) between the selected template atom A (2, 1) and the compared atom A (1, 1) is calculated.

The atomic distance is given by the following general formula (1):

$$r = \sqrt{(x1-x2)^2 + (y1-y2)^2 + (z1-z2)^2} \quad (1)$$

x1, y1 and z1: coordinates of a compared atom
x2, y2 and z2: coordinates of a template atom In Step 4, it is determined if the atomic distance r (21, 11) calculated in Step 3 is not greater than a first threshold (upper threshold) rlim 1 (1, 1) specific to the template atom A (2, 1) and the compared atom A (1, 1). Preferably used as the first threshold rlim 1 (1, 1) is a value derived by multiplying the mean of van der Waals radii vdw [A (2,1)] of the selected template atom A (2, 1) and vdw [A (1,1)] of the compared atom A (1, 1) by a predetermined first constant k1. The first threshold rlim 1 (1, 1) can be calculated in the above-mentioned Step 3.

$$r\lim(1, 1) = k1 \cdot \frac{vdw[A(2, 1)] + vdw[A(1, 1)]}{2} \quad (2)$$

The first threshold may be selected from the van der Waals radius of one of the two atoms, a larger van der Waals radius of those of the two atoms, a smaller van der Waals radius of those of the two atoms, or values derived by multiplying these van der Waals radii by the first constant.

When the difference in X, Y or Z coordinate between the template atom and the atom to be compared (e.g. x21−x11, y21−y11, or z21−z11) is greater than the first threshold rliml (1, 1), the atomic distance between the two atoms in the three-dimensional space is naturally greater than the first threshold rlim 1 (1, 1). Therefore, before the calculation of the atomic distance, the difference in X, Y or Z coordinate between the template atom and the compared atom (e.g. x21−x11, y21−y11, or z21−z11) is calculated. Then, only when the differences in all the three coordinates are equal to or smaller than the first threshold rlim 1 (1, 1), the atomic distance is calculated. This method minimizes calculations, increases the calculation speed, and reduces required memories.

When the atomic distance exceeds the first threshold rlim 1 (1, 1), the following Steps 5 and 6 will be skipped. When the atomic distance is not greater than the first threshold rlim 1 (1, 1), the procedure goes to next Step 5.

In Step 5, it is determined if the atomic distance r (21, 11) calculated in Step 3 is not greater than a second threshold (lower threshold) rlim 2 (1, 1) specific to the template atom A (2, 1) and the compared atom A (1, 1). An example of the second threshold rlim 2 (1, 1) is a value derived by multiplying the mean of the van der Waals radii of the selected template atom A (2, 1) and the compared atom A (1, 1) by a predetermined second constant k2, as shown in the following equation (3). The second threshold rlim 2 (1, 1) can be calculated in the above-mentioned Step 3. The second constant k2 is a value smaller than the first constant k1 used to obtain the first threshold rlim 1 (1, 1).

$$r\lim2(1, 1) = k2 \cdot \frac{vdw[Atom(2, 1)] + vdw[Atom(1, 1)]}{2} \quad (3)$$

The second threshold can be selected from the van der Waals radius of one of the two atoms, a larger van der Waals radius of those of the two atoms, a smaller van der Waals radius of those of the two atoms, or values derived by multiplying these van der Waals radii by the predetermined second constant.

As known, the van der Waals radius is a value specific to each atom. Thus, the first and second thresholds vary with the types of the two atoms to be calculated.

Responsive to the determination results in Steps 4 and 5, the process of the program branches to the routes shown in the following table.

TABLE 2

| Branch condition | Branch destination | Processing |
| --- | --- | --- |
| rlim1 < r | S7 | si, sitemp: unchanged |
| rlim2 ≦ r < rlim1 | S11 | sitemp ← 0.5 |
| r ≦ rlim2 | S6 | si ← si + 1 |

In the table, "si" is a parameter showing the degree of superimposition of a template molecule and a compared molecule, i.e. similarity between the both molecules. The higher similarity index indicates the higher similarity between the both molecules. "Sitemp" is a parameter showing the correlation between a selected template atom and a compared atom. The sum of the correlation coefficients "sitemp" obtained for each of all the template atoms corresponds to the similarity "si" between the template molecule and the compared molecule. The similarity index "si" and correlation coefficient "sitemp" are reset to a initial value of 0 in any one of the steps before Step 3 (e.g. Step 2).

Branch processing will be specifically described. For example, suppose that it has been determined that the atomic distance r (21, 11) exceeds the first threshold (upper threshold) rlim 1 (1, 1). In this case, the template atom A (2, 1) is at a distance from the compared atom A (1, 1) in the three-dimensional space, and thus the template atom A (2, 1) and the compared molecule M (1) have little correlation. Therefore, the similarity index "si" and correlation coefficient "sitemp" do not change.

When the atomic distance r (21, 11) is not greater than the first threshold rlim 1 (1, 1) and exceeds the second threshold rlim 2 (1, 1), the template atom A (2, 1) is relatively in proximity to the compared atom A (1, 1) in the three-dimensional space. This proximity is a factor in increasing the correlation and similarity between the template molecule M (2) and compared molecule M1 (1). Thus, a predetermined low score (e.g. 0.5) is given to the correlation coefficient "sitemp" in Step 6.

When the atomic distance r (21, 11) is not greater than the second threshold rlim 2 (1, 1), the template atom A (2, 1) is in close proximity to the compared atom A (1, 1) in the three-dimensional space. This close proximity is a large factor in increasing the correlation and similarity between the template molecule M (2) and compared molecule M1 (1). Thus, a predetermined high score (e.g. 1) is given to the similarity index "si" in Step 11.

When the template atom A (2, 1) is in close proximity to the compared atom A (1, 1) in the three-dimensional space (i.e. when a high score of 1 is added to the similarity index "si"), it is appropriate to consider that the atomic distances between the selected template atom A (2, 1) and the other compared atoms A (1, 2) and A (1, 3) are not smaller than the atomic distance between the template atom A (2, 1) and the compared atom A (1, 1). Therefore, in this case, the atomic distances between the template atom A (2, 1) and the other compared atoms A (1, 2) and A (1, 3) are not calculated. Then, no change is added to the correlation coefficient "sitemp" between the selected template atom and the compared molecule, a high score of 1 is added to the similarity index "si" thereof, and the calculations of the atomic distance with respect to the template atom is completed.

Even when the template atom A (2, 1) is relatively in proximity to the compared atom A (1, 1), it is possible that another template atom A (2, 2), A (2, 3) or A (2, 4) may be much closer to the compared atom A (1, 1). Therefore, in this case, no change is added to the similarity index "si", and a low score of 0.5 is temporarily given to the correlation coefficient "sitemp".

However, the high sore value and low score value are not limited to 1 and 0.5, respectively. Such values may be set by a user of this program as required.

When a high score of 1 is added to the similarity index "si" in Step 11, the two atoms A (2, 1) and A (1, 1) are in close proximity to each other in the space coordinates. Thus, the atomic distances between the atom A (2, 1) and the other compared atoms A (1, 2) and A (1, 3) need not be calculated. Then, the procedure goes to the calculations of the atomic distance between the other template atom A (2, 2) in the template molecule M (2) and the atom A (1, 1) in the compared molecule M (1).

When a low score of 0.5 is given to the correlation coefficient "sitemp" in Step 6, the procedure goes to Step 7. In Step 7, it is determined whether the operations in the above-mentioned Steps 3 to 6 have been completed between the selected template atom A (2, 1) and the other compared atoms A (1, 2) and (1, 3). When the above-mentioned steps are not completed for all the atoms in the compared molecule, the process returns to Step 3 and the next compared atom A (1, 2) is selected from the first molecule M (1). The above-mentioned steps are repeated for this selected compared atom A (1, 2). When it is determined that the atomic distance r (21, 12) is equal to or smaller than the first threshold rlim 1 (1, 2) and second threshold rlim 2 (1, 2), a high score of 1 is added to the similarity index "si". The atomic distance between the template atom A (2, 1) and the remaining compared atom A (1, 3) is not calculated. The procedure goes to the calculations of the atomic distance between the other template atom A (2, 2) and each atom in the compared molecule.

Similar to the compared atoms A (1, 1) and A (1, 2), when it has been determined that the atomic distance r (21, 13) between the compared atom A (1, 3) and the template atom A (2, 1) is not greater than the first threshold rlim 1 (1, 3) and exceeds the second threshold rlim 2 (1, 3), a predetermined low score of 0.5 is added to the correlation coefficient "sitemp". In other words, the correlation coefficient "sitemp" is kept to 0.5. However, when it has been determined that the atomic distance r (21, 13) is not greater than the first threshold rlim 1(1, 3) and the second threshold rlim 2 (1, 3), a high score of 1 is added to the similarity index "si".

As described above, the operations in Steps 4 to 7 are repeated for a selected template atom and each of the compared atoms. During the operation, when it is determined that the atomic distance therebetween is not greater than the first threshold and exceeds the second threshold, the correlation coefficient "sitemp" with respect to the selected template atom is kept to a low score of 0.5. Once a low score of 0.5 is given to the correlation coefficient "sitemp" with respect to the selected template atom, the low score is kept even when it is determined that the atomic distance is not greater than the first threshold and exceeds the second threshold, or even when it is determined that the atomic distance exceeds the first threshold, in the process of calculations with respect to the selected template atom. However, when the atomic distance with respect to the template atom is not greater than the first and second thresholds, a high score of 1 is added to the similarity index "si".

After it is determined in Step 7 that the calculations of the atomic distances between the selected template atom and all the compared atoms have been completed, the correlation coefficient "sitemp" (a low score of 0.5) is added to the similarity index "si" in Step 8. Next, in Step 9, the correlation coefficient "sitemp" is reset to "0" to prepare for the calculations for a next template atom to be selected.

In step 10, it is determined whether the above-mentioned operations have been completed for all the template atoms A (2, 1) to A (2, 4) in the template molecule M (2). When the operations have not been completed yet, another atom in the template molecule is selected in Step 12 and the process returns to step 3 (refer to FIGS. 3 and 4).

With the operations in Steps 3 to 11, the similarity index "si" of the two molecules with respect to a configuration in the three-dimensional space is calculated.

Next, in Step 12, it is determined whether or not the similarity index "si" obtained with respect to a configuration in the three-dimensional space is the maximum value. When it is determined that the similarity index is not the maximum value, the relative position of the first and second molecules in the three-dimensional space is changed (e.g. by rotations and translations) and then the above-mentioned operations are repeated. The movements of the first and second molecules include rotations with respect to three (i.e. X, Y, and Z) axes or axes parallel to the three axes as well as translations in the directions parallel to the three axes. It is a very important technique to move the molecules so that the similarity index "si" thereof is maximized. Such a technique includes the simplex optimization described in Nelder, J. A., and Mead, R. 1965, Computer Journal, vol. 7, p.308. An example of the source codes thereof is described in the Numerical Recipes in C: The Art of Scientific Computing, The Press Syndicate of the University of Cambridge (Japanese version: the Numerical Recipes in C, Gijyutu-Hyoron Co., Ltd.).

In the above description, the first and second thresholds are determined according to the van der Waals radii of the atoms. However, values derived from the atomic radii, covalent radii, and combination thereof can be used other than the van der Waals radii.

The coordinate values are not necessarily represented by the Cartesian coordinate system. They can be represented by spherical coordinates. In this case, the three-dimensional space is given by spherical coordinates.

Moreover, when the molecular similarity evaluation method proposed by Meyer or Richards et al. is applied to the configurations of the molecules for which the maximum similarity index has been obtained in the above-mentioned manner, the molecular similarity can more 5 accurately be evaluated. Refer to Journal of Computer-Aided Molecular Design, 5 (1991), 427–439, "Similarity of molecular shape", and the Perspectives in Drug Discovery and Design, 9/10/11:321–338, 1998, "Explicit Calculation of 3D Molecular Similarity".

[Preferred Embodiment 1]

A concrete preferred embodiment of the similarity evaluation will be described hereinafter.

Figure 6:
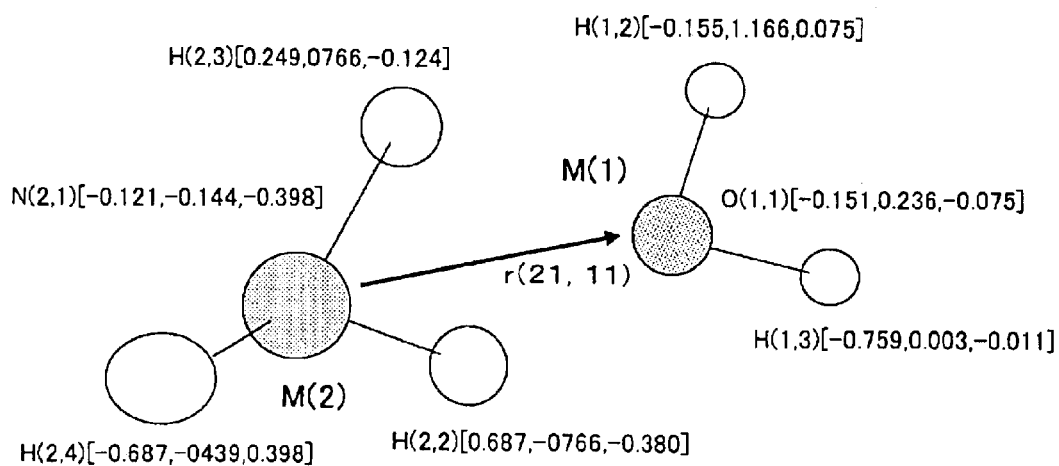
FIG. 6 is a drawing for illustrating molecular models between which similarity is evaluated in a first preferred embodiment of the present invention.
Figure 7:
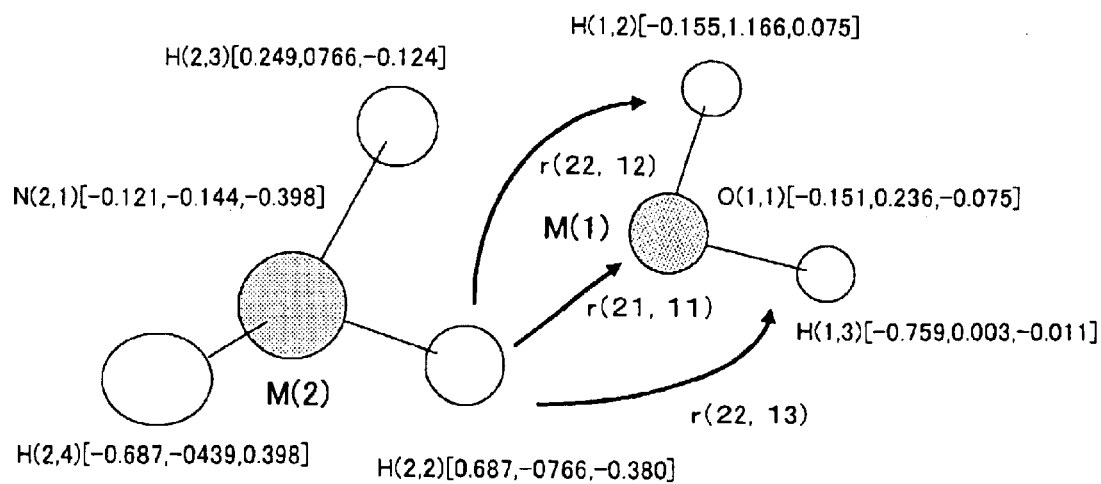
FIG. 7 is a drawing for illustrating the molecular models between which similarity is evaluated in the first preferred embodiment together with FIG. 6.

1. Subject of Evaluation:

For better understanding of the present invention, similarity evaluation is performed between a water molecule M (1) and an ammonia molecule M (2) having simple molecule structures as shown in FIGS. 6 and 7. The water molecule M (1) has three atoms. The ammonia molecule M (2) has four atoms. Therefore, the ammonia molecule M (2) is a template molecule and the water molecule M (1) is a compared molecule.

2. Coordinate of Atom

The three-dimensional data (e.g. three-dimensional coordinate, atomic distance, and bond angle) of the atoms included in the water molecule and ammonia molecule is generated by such a molecule editor as the CHEM3D® (a registered trademark of CambridgeSoft Corporation). After the generation of the data, calculations of molecular force fields, such as MM2 and AMBER, and calculations of molecular orbital, such as MOPAC, may be performed so that the most stable structures of the molecules are obtained. In addition, the three-dimensional structures of molecules registered in the Protein Data Bank (PDB) or the like may be used. For taxol, the coordinates in the WebLab ViewerLite (MSI) is used. For FK-506, the coordinates downloaded from the PDB are used. The structures of the water and ammonia molecules are generated using the Chem3D.

3. Disposition of Molecules

A water molecule and an ammonia molecule are disposed in a three-dimensional coordinate system according to the obtained three-dimensional coordinates thereof, as shown in FIG. 6.

The coordinates of the atoms disposed are shown in Table 3. The unit of all the coordinate values used in Table 3 and the following description is Å.

TABLE 3

| | | [unit: Å] | | |
|---|---|---|---|---|
| Molecule | Atom | X coordinate | Y coordinate | Z coordinate |
| Water: M (1) | O (1, 1) | −0.151 | +0.236 | −0.075 |
| | H (1, 2) | −0.155 | +1.166 | +0.075 |
| | H (1, 3) | +0.759 | +0.003 | −0.011 |
| Ammonia: M (2) | N (2, 1) | −0.121 | −0.144 | −0.398 |
| | H (2, 2) | +0.687 | −0.766 | −0.380 |
| | H (2, 3) | +0.249 | +0.766 | −0.124 |
| | H (2, 4) | −0.687 | −0.439 | +0.398 |

4. Similarity Evaluation

The similarity of each atom in the ammonia molecule, i.e. a template molecule, with respect to each atom in the water molecule is obtained. Specifically, the following steps (operations) are performed.

(1) Step 1

The distance between a nitride atom N (2, 1) and an oxygen atom O (1, 1) is compared with a first threshold rlim 1 (21, 11). The first threshold is determined according to the van der Waals radii of these two atoms with respect to one of X, Y, and Z coordinates.

The first threshold is given as a value derived by multiplying the mean of the van der Waals radius [vdw] of each atom to be calculated by a first constant k1=1.3. However, the first constant is not limited to this value. Specifically, the van der Waals radius [vdw (N)] of the nitride atom N (2, 1) and the van der Waals radius [vdw (O)] of the water atom O (1, 1) are given as shown in the following equations (4) and (5), respectively. Thus, the first threshold rlim 1 (21, 11) is calculated as shown in the equation (6).

$$vdw(N)=1.54 \tag{4}$$

$$vdw(O)=1.40 \tag{5}$$

$$r\text{lim}1(21, 11) = 1.3 \cdot \left(\frac{1.54 + 1.40}{2}\right) = 1.91 \tag{6}$$

Next, as shown in the following equations (7) to (9), the differences in X, Y and Z coordinates between the nitride atom N (2, 1) and oxygen atom O (1, 1) are obtained. The equations (7) to (9) also include the comparison with the first threshold rlim 1 (1, 1).

$$Abs(x2-x1)=-0.121-(-0.151)=0.030<1.911 \tag{7}$$

$$Abs(y2-y1)=-0.144-(+0.236)=0.380<1.911 \quad (8)$$

$$Abs(z2-z1)=-0.398-(-0.075)=0.323<1.911 \quad (9)$$

As obvious from the equations (7) to (9), the differences in X, Y and Z coordinates between the nitride atom N (2, 1) and oxygen atom O (1, 1) are not greater than the first threshold rlim1 (1, 1). Therefore, the distance r (21, 11) between the nitride atom N (2, 1) in the ammonia molecule M (2) and the oxygen atom O (1, 1) in the water molecule M (1) is computed. Since the three-dimensional coordinates of the nitride atom N (2, 1) and oxygen atom O (1, 1) are known, the atomic distance r (21, 11) therebetween is obtained using the three-dimensional coordinates, as shown in the following equation (10).

$$r(21, 11) = \sqrt{(0.030)^2 + (0.38)^2 + (0.323)^2} = 0.05 \quad (10)$$

The calculated atomic distance r (21, 11) is compared with a second threshold. The second threshold rlim 2 (21, 11) is given as a value derived by multiplying the mean of the van der Waals radius of each atom to be calculated by a second constant k2=0.6. However, the second constant is not limited to this value. Specifically, the second threshold rlim 2 (21, 11) is calculated as shown in the following equation (11).

$$r\text{lim}2(21, 11) = 0.6 \cdot \left(\frac{1.54 + 1.40}{2}\right) = 0.882 \quad (11)$$

The relation of the atomic distance r (21, 11) between the nitride atom N (2, 1) and the oxygen atom O (1, 1) with respect to the first threshold rlim 1 (21, 11) and the second threshold rlim 2 (21, 11) obtained in the above-mentioned manner is represented by the following inequality (12).

$$r(21,11)=0.500<r\text{lim}2(21,11)=0.882<r\text{lim}1(21,11)=1.911 \quad (12)$$

Thus, a high score of 1 is given to the similarity index "si" of the nitride atom N (2, 1) and oxygen atom O (1, 1). In this case, the atomic distance between the nitride atom N (2, 1) and another hydrogen atom H (1, 2) or H (1, 3) is not calculated. The procedure goes to the calculations of the atomic distances between a hydrogen atom H (2, 2) in the ammonia molecule M (2) and each atom in the water molecule.

(2) Step 2

[1] As shown in the following equations (13) to (15), the differences in X, Y and Z coordinates between the hydrogen atom H (2, 2) in the ammonia molecule M (2) and the oxygen atom O (1, 1) in the water molecule M (1) are obtained.

$$Abs(x2-x1)=+0.687-(-0.151)=0.838 \quad (13)$$

$$Abs(y2-y1)=-0.766-(+0.236)=1.002 \quad (14)$$

$$Abs(z2-z1)=-0.380-(-0.075)=-0.305 \quad (15)$$

The obtained differences in the coordinates are compared with the first threshold rlim 1 (22, 11) and the second threshold rlim 2 (22, 11). The first threshold rlim 1 (22, 11) and the second threshold rlim 2 (22, 11) are calculated as shown in the following equations (16) and (17), respectively.

$$r\text{lim}1(22, 11) = 1.3 \cdot \left(\frac{1.20 + 1.40}{2}\right) = 1.690 \quad (16)$$

$$r\text{lim}2(22, 11) = 0.6 \cdot \left(\frac{1.20 + 1.40}{2}\right) = 0.780 \quad (17)$$

As obvious from the calculation results, each difference in any coordinate (0.838, 1.002, −0.305) is not greater than the first threshold rlim 1 (22, 11)=1.690. Therefore, the atomic distance r (22, 11) between the hydrogen atom H (2, 2) and the oxygen atom O (1, 1) is calculated as shown in the following equation (18).

$$r(22, 11) = \sqrt{(0.838)^2 + (1.002)^2 + (0.305)^2} = 1.340 \quad (18)$$

The relation of the atomic distance r (21, 11) with respect to the first threshold rlim 1 (21, 11) and the second threshold rlim 2 (21, 11) obtained by the calculations is represented by the following inequality (19).

$$r\text{lim}2(22,11)=0.78<r(22,11)=1.340<r\text{lim}1(22,11)=1.690 \quad (19)$$

Therefore, "0.5" is given to the correlation coefficient "sitemp (2)" of the hydrogen atom H (2, 2).

In a manner similar to Step 2, the relation of the hydrogen atom H (2, 2) in the ammonia molecule M (2) with respect to the hydrogen atom H (1, 2) in the water molecule M (1) is determined. In the following description, each explanation of each calculation is minimized for simplicity.

First, the differences in X, Y and Z coordinates between the hydrogen atom H (2, 2) in the ammonia molecule M (2) and the hydrogen atom H (1, 2) in the water molecule M (1) are obtained, as shown in the following equations (20) to (22).

$$Abs(x2-x1)=+0.687-(-0.155)=0.842 \quad (20)$$

$$Abs(y2-y1)=-0.766-(+1.116)=1.822 \quad (21)$$

$$Abs(z2-z1)=-0.380-(+0.075)=-0.455 \quad (22)$$

The first threshold rlim 1 (22, 12) and the second threshold rlim 2 (22, 12) are calculated as shown in the following equations (23) and (24).

$$r\text{lim}1(22, 12) = 1.3 \cdot \left(\frac{1.20 + 1.20}{2}\right) = 1.560 \quad (23)$$

$$r\text{lim}2(22, 12) = 0.6 \cdot \left(\frac{1.20 + 1.20}{2}\right) = 0.720 \quad (24)$$

As obvious from the calculation results, the difference in Y coordinate (1.822) is greater than the first threshold rlim 1 (22, 12)=1.560. Therefore, the correlation coefficient "sitemp (2)" is kept to "0.5" and the procedure goes to the next operation.

[3] In a similar manner, the relation of the hydrogen atom H (2, 2) in the ammonia molecule M (2) with respect to the hydrogen atom H (1, 3) in the water molecule M (1) is determined.

First, the differences in X, Y and Z coordinates between the hydrogen atom H (2, 2) and the hydrogen atom H (1, 3) in the water molecule M (1) are obtained, as shown in the following equations (25) to (27).

$$Abs(x2-x1)=+0.687-(+0.759)=-0.072 \quad (25)$$

$$Abs(y2-y1)=-0.766-(+0.003)=-0.769 \quad (26)$$

$$Abs(z2-z1) = -0.380 - (-0.011) = -0.369 \quad (27)$$

The first threshold rlim 1 (22, 13) and the second threshold rlim 2 (22, 13) are calculated as shown in the following equations (28) and (29).

$$r\lim 2(22, 13) = 1.3 \cdot \left(\frac{1.20 + 1.20}{2}\right) = 1.560 \quad (28)$$

$$r\lim 2(22, 13) = 0.6 \cdot \left(\frac{1.20 + 1.20}{2}\right) = 0.720 \quad (29)$$

All the differences in X, Y and Z coordinates are equal to or smaller than the first threshold rlim 1 (22, 13). Thus, the atomic distance r (22, 13) is obtained as shown in the following equation (30).

$$r(22, 13) = \sqrt{(0.072)^2 + (0.769)^2 + (0.369)^2} = 0.856 \quad (30)$$

The relation of the atomic distance r (22, 13) with respect to the first threshold rlim 1 (22, 13) and the second threshold rlim 2 (22, 13) is represented by the following inequality (31).

$$rlim2(22,13) = 0.72 < r(22,13) = 0.856 < rlim1(22,13) = 1.560 \quad (31)$$

Therefore, "0.5" is still given to the correlation coefficient "sitemp (2)" of the hydrogen atom H (2, 2).

(3) Step 3

In a similar manner, a correlation coefficient "sitemp (3)" of a hydrogen atom H (2, 3) in the ammonia molecule M (2) with respect to each atom in the water molecule M (1) is determined. The process of calculations is omitted. As a result of the calculations, the correlation coefficient "sitemp (3)"=1.

(4) Step 4

In a similar manner, a correlation coefficient "sitemp (4)" of a hydrogen atom H (2, 4) in the ammonia molecule M (2) with respect to each atom in the water molecule M (1) is determined. The process of calculations is omitted. As a result of the calculations, correlation coefficient "sitemp (4)"=0.5.

(5) Step 5

The correlation coefficients "sitemp" obtained in Steps 1 to 4 are summed up and the similarity index "si" is calculated as shown in equation (32).

$$si = sitemp(1) + sitemp(2) + sitemp(3) + sitemp(4) = 1 + 0.5 + 1 + 0.5 = 3 \quad (32)$$

(6) Step 6

After the position of the water molecule with respect to the ammonia molecule is moved by a predetermined amount in the three-dimensional space, the similarity index "si" is calculated according to the above-mentioned Steps 1 to 5. The movements of the molecule include translations in parallel with coordinate axes and rotations. For example, the water molecule is moved with respect to the ammonia molecule in a plurality of directions. Then, the correlation coefficients in each case are calculated. Next, on the basis of the calculation results, the water molecule is moved in a direction in which a higher correlation efficient is obtained. After repetition of these operations, the calculations are completed when the maximum value of the similarity index "si" is obtained. Then, as shown in the following equation (33), the similarity between the water and ammonia molecules "SI" is determined by dividing the maximum the similarity index "si" by the number of atoms in the template molecule "Nmol".

$$SI = \frac{si}{Nmol} \quad (33)$$

[Second Preferred Embodiment]

(1) Optimization of Constants

Aldosterone (20 conformations) were used as both template molecule and compared molecule. The compared molecule was moved in steps of 0.15 Å in a three-dimensional space. The similarity between the molecules was calculated using the evaluation method of the present invention. The calculation results were compared with those obtained by the method by Meyer et al. (method M) and the method by Richards et al. (method R) and thereby, constants required for threshold calculations (first and second constants) were determined. The calculation results are shown in the following table.

TABLE 4

| | Optimum constants | | | | | | | | | | |
|---|---|---|---|---|---|---|---|---|---|---|---|
| k1 | 1.3 | 1.1 | 1.2 | 1.3 | 1.3 | 1.0 | 1.1 | 1.2 | 1.0 | Method M | Method R |
| k2 | 0.5 | 0.6 | 0.6 | 0.6 | 0.6 | 0.7 | 0.7 | 0.7 | 0.8 | | |
| k3 | .974 | .984 | .984 | .987 | .986 | .979 | .982 | .982 | .981 | (1.) | .993 |

Table 4 shows that the highest similarity index "SI" could be obtained when a first constant k1 was set to 1.3 and a second constant k2 was set to 0.6. However, similarity indices equal to or higher than 0.97 can be obtained even when the first constant k1 is arbitrarily changed within a range of 1.0 to 1.3 and the second constant k2 is arbitrarily changed within a range of 0.5 to 0.8.

(2) Comparison Between Methods

Figure 8:
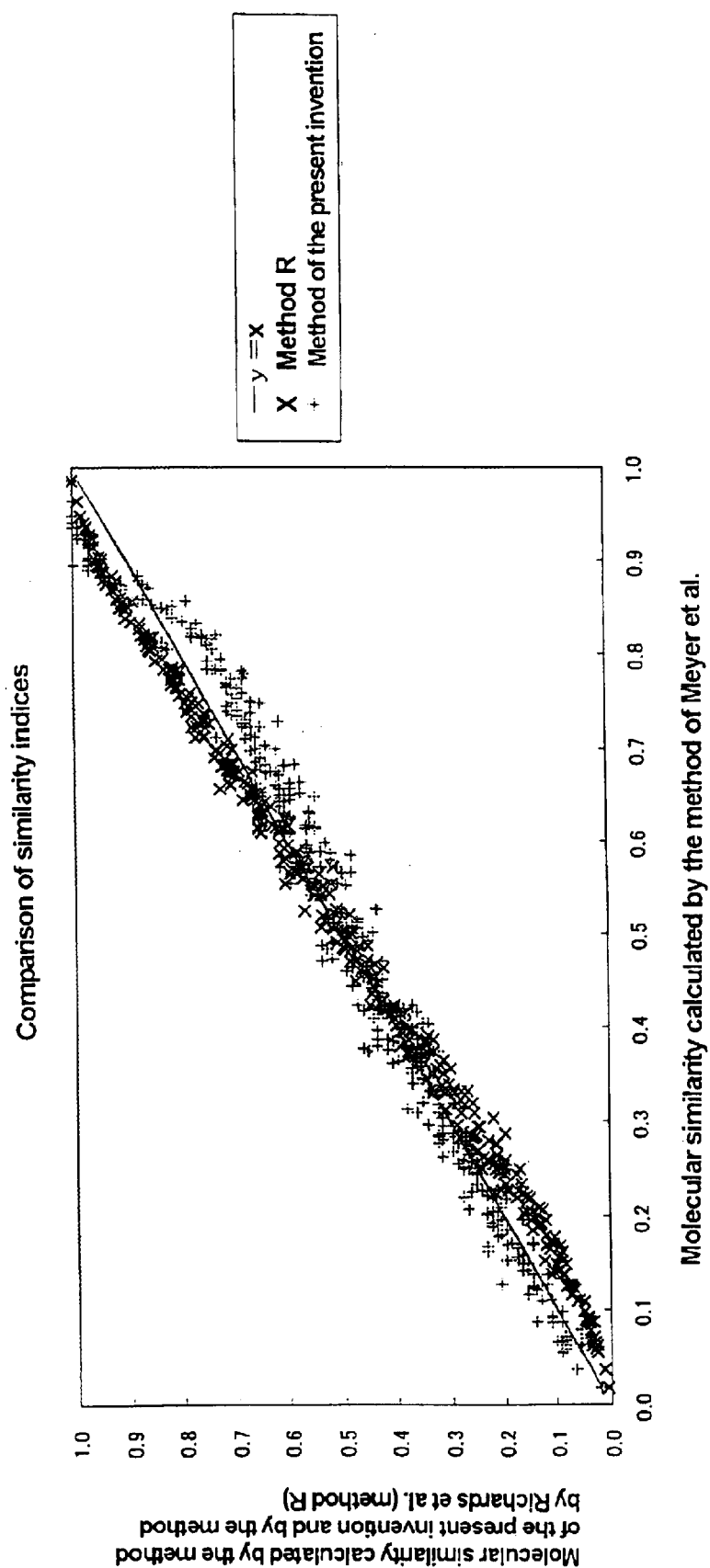
FIG. 8 is a graph showing evaluation results of a second preferred embodiment of the present invention.

Calculation results of similarity between a template aldosterone molecule and 400 randomly oriented conformations of another aldosterone molecule were compared using the optimized constants (k1=1.3 and k2=0.6). The calculation results are shown in Table 5 and FIG. 8.

TABLE 5

| | Similarity and standard deviation | | |
|---|---|---|---|
| | Present invention | Method M | Method R |
| Similarity: SI | 0.971 | (1.000) | 0.977 |
| Standard deviation: SD | 0.043 | (0.000) | 0.038 |

As obvious from the comparison in calculation results between the method of the present invention and the method R shown in the table, the method of the present invention can provide calculation results similar to those obtained by the method R.

(3) Superimposition of Taxol Molecules

Two taxol molecules were superimposed on each other using the simplex optimization in accordance with the method of the present invention (A), the method M (B), the method R (C), and combination of the method of the present invention and the method R (D). The results are shown in Table 6.

TABLE 6

Comparison of superimposed taxol using the simplex optimization between the methods

| | Present invention (A) | Meyer (B) | Richards (C) | (A) + (C) |
|---|---|---|---|---|
| Final similarity index | 0.938 (0.919) | 0.986 | 1.000 | 1.000 |
| Iterations | 1,219 | 1,743 | 3,533 | 1,285 |
| Calculation time (sec.) | 2.15 | 18,783.86 | 1,003.16 | 20.62 |
| Ratio | $1.15 \times 10^{-4}$ | 1.00 | $5.35 \times 10^{-1}$ | $1.10 \times 10^{-2}$ |
| Calculation time/ iteration (sec.) | 0.002 | 10.777 | 0.284 | — |

The final similarity index in the parentheses shows similarity index of the optimized conformation calculated by method R (C), after the superimposition of the molecules are optimized by the method of the present invention.

As obvious from Table 6, the method of the present invention can attain calculations as approx. five thousand times as fast as the method M and as approx. one hundred times as fast as the method R.

(4) Superimposition of FK-506 Molecules

FK-506 molecules were superimposed on each other in a similar manner. The results are shown in Table 7.

TABLE 7

Comparison of superimposed FK-506 using the simplex optimization between the methods

| | Present invention (A) | Meyer (B) | Richards (C) | (A) + (C) |
|---|---|---|---|---|
| Final similarity index | 1.000 (0.961) | 0.985 | 0.996 | 1.000 |
| Iterations | 1,217 | 1,579 | 2,674 | 1,269 |
| Calculation time (sec.) | 3.09 | 18,257.80 | 1,109.01 | 29.02 |
| Ratio | $1.69 \times 10^{-4}$ | 1.00 | $6.07 \times 10^{-2}$ | $1.59 \times 10^{-3}$ |
| Calculation time/ iteration (sec.) | 0.003 | 11.563 | 0.415 | — |

An advantage similar to that obtained with taxol was confirmed.

In the above description, the molecular similarity evaluation method of the present invention is applied to a shape similarity evaluation, as an example. However, the present invention is applicable to molecular similarity evaluation methods using electrostatic capacity, hydrogen bond and hydrophobic property.

As obvious from the above description, the molecular similarity evaluation method and program of the present invention can evaluate similarity between two molecules with a calculation time and amount less than those taken by the method by Meyer et al. and the method by Richards et al., and with a similar degree of accuracy.

It should be noted that the present application is based upon Japanese Patent Application No. 2000-129216 which is entirely incorporated herein by reference.

What is claimed is:

1. A molecular similarity evaluation method of evaluating similarity between a first molecule and a second molecule, comprising steps of:
    (a) obtaining an upper threshold and a lower threshold from one of a value specific to an atom included in said first molecule, a value specific to an atom included in said second molecule of which correlation with respect to said atom in said first molecule is to be evaluated, or another value obtained from these values;
    (b) calculating correlation between said atom in said first molecule and said atom in said second molecule, using said upper and lower thresholds; and
    (c) evaluating similarity between said first and second molecules based on said correlation obtained in the step (b).

2. A molecular similarity evaluation method of obtaining correlation between each atom included in a first molecule and each atom included in a second molecule based on an atomic distance therebetween and evaluating similarity between said first and second molecules based on this correlation, wherein operation of obtaining correlation between two atoms includes steps of:
    (a) obtaining a value specific to an atom in said first molecule and/or an atom in said second molecule;
    (b) obtaining an upper threshold from said specific value obtained in the step (a);
    (c) obtaining a lower threshold from said specific value obtained in the step (a);
    (d) obtaining a distance between said two atoms; and
    (e) evaluating correlation between said atom in said first molecule and said atom in said second molecule, using said atomic distance obtained in the step (d), said upper threshold, and said lower threshold.

3. A molecular similarity evaluation method of evaluating similarity between a first molecule and a second molecule disposed in a three-dimensional coordinate system, comprising steps of:
    (a) resetting a correlation coefficient;
    (b) selecting one atom from a plurality of atoms included in said second molecule;
    (c) selecting one atom from a plurality of atoms included in said first molecule;
    (d) obtaining an upper threshold and a lower threshold from a value specific to both or one of said atoms selected in each of the steps (b) and (c);
    (e) obtaining a distance between said atoms selected in each of the steps (b) and (c);
    (f) obtaining a correlation coefficient according to said atomic distance obtained in the step (e), based on said upper and lower thresholds obtained in the step (d);
    (g) determining whether or not any atom unselected from said plurality of atoms included in said first molecule exists, after completion of the step (f);
    (h) when it is determined in the step (g) that any atom unselected from said plurality of atoms included in said first molecule exists, returning to the step (c), selecting another unselected atom from said plurality of atoms in said first molecule, executing the steps (d) through (f), and updating said correlation coefficient; and
    (i) when it is determined in the step (g) that any atom unselected from said plurality of atoms included in said first molecule does not exist, returning to the step (a), selecting another unselected atom from said plurality of atoms in said second molecule, executing the steps (c) through (h), and adding said correlation coefficient.

4. The molecular similarity evaluation method as set forth in claim 3, wherein said atomic distance obtained in the step (e) is a distance with respect to one of axes in Cartesian coordinate system.

5. A molecular similarity evaluation method of evaluating similarity between two molecules, comprising steps of:
(a) obtaining a three-dimensional coordinate of each atom included in first and second molecules;
(b) disposing said first and second molecules in a three-dimensional coordinate system;
(c) obtaining a similarity index of each atom included in said second molecule with respect to each atom included in said first molecule, comprising sub-steps of:
(c-0) resetting a correlation coefficient;
(c-1) selecting one atom from a plurality of atoms included in said second molecule;
(c-2) selecting one atom from a plurality of atoms included in said first molecule;
(c-3) obtaining an upper threshold and a lower threshold from a value specific to both or one of said atoms selected in each of the sub-steps (c-1) and (c-2);
(c-4) obtaining a distance between said atoms selected in each of the sub-steps (c-1) and (c-2);
(c-5) obtaining a correlation coefficient according to said atomic distance obtained in the sub-step (c-4), based on said upper and lower thresholds obtained in the sub-step (c-3);
(c-6) determining whether or not any atom unselected from said plurality of atoms included in said first molecule exists, after completion of the sub-step (c-5);
(c-7) when it is determined in sub-step (c-6) that any atom unselected from said plurality of atoms included in said first molecule exists, returning to the sub-step (c-2), selecting another unselected atom from said plurality of atoms in said first molecule, executing the sub-steps (c-3) through (c-6), and updating said correlation coefficient; and
(c-8) when it is determined in the sub-step (c-6) that any atom unselected from said plurality of atoms included in said first molecule does not exist, returning to step (c-0), selecting another unselected atom from said plurality of atoms in said second molecule, executing the sub-steps (c-2) through (c-7), and adding said correlation coefficient so as to obtain said similarity index; and
(d) changing a relative position of said first molecule and said second molecule in the three-dimensional coordinate system, after the completion of the step (c).

6. The molecular similarity evaluation method as set forth in claim 5, wherein said atomic distance obtained in the sub-step (c-4) is a distance with respect to one of axes in Cartesian coordinate system.

7. The molecular similarity evaluation method as set forth in claim 5, wherein, in the step (d), said relative position of said first and second molecules is changed in a direction to improve said similarity index.

8. The molecular similarity evaluation method as set forth in claim 1, wherein one of a van der Waals radius, atomic radius, and covalent radius of said atom can be a value specific to said atom.

9. The molecular similarity evaluation method as set forth in claim 1, wherein said upper threshold is obtained by multiplying a value specific to said atom by an upper limit constant.

10. The molecular similarity evaluation method as set forth in claim 1, wherein said lower threshold is obtained by multiplying a value specific to said atom by a lower limit constant.

11. The molecular similarity evaluation method as set forth in claim 9, wherein said upper limit constant is a value ranging from 1.0 to 1.3.

12. The molecular similarity evaluation method as set forth in claim 10, wherein said lower limit constant is a value ranging from 0.5 to 0.8.

13. A molecular similarity evaluation program for evaluating similarity between a first molecule and a second molecule disposed in a three-dimensional coordinate system, causing a computer to execute operations of:
(a) resetting a correlation coefficient;
(b) selecting one atom from a plurality of atoms included in said second molecule;
(c) selecting one atom from a plurality of atoms included in said first molecule;
(d) obtaining an upper threshold and a lower threshold from a value specific to both or one of said atoms selected in each of the operations (b) and (c);
(e) obtaining a distance between said atoms selected in each of the operations (b) and (c);
(f) obtaining a correlation coefficient according to said atomic distance obtained in the operation (e), based on said upper and lower thresholds obtained in operation (d);
(g) after completion of the operation (f), returning to the operation (c), selecting another unselected atom from said plurality of atoms included in said first molecule, executing the operations (d) through (f) on said another atom selected in this operation, and updating said correlation coefficient; and
(h) after completion of the operation (g), returning to the operation (a), selecting another unselected atom from said plurality of atoms in said second molecule, executing the operations (c) through (h) on said another atom selected in this operation, and adding said correlation coefficient.

14. The molecular similarity evaluation program as set forth in claim 13, wherein said atomic distance obtained in the operation (e) is a distance with respect to one of axes in Cartesian coordinate system.

15. A molecular similarity evaluation program for evaluating similarity between two molecules, program causing a computer to execute operations of:
(a) obtaining a three-dimensional coordinate of each atom included in first and second molecules;
(b) disposing said first and second molecules in a three-dimensional coordinate system;
(c) obtaining a similarity index of each atom included in said second molecule with respect to each atom included in said first molecule, including sub-operations of:
(c-0) resetting a correlation coefficient;
(c-1) selecting one atom from a plurality of atoms included in said second molecule;
(c-2) selecting one atom from a plurality of atoms included in said first molecule;
(c-3) obtaining an upper threshold and a lower threshold from a value specific to both or one of said atoms selected in each of the sub-operations (c-1) and (c-2);
(c-4) obtaining a distance between said atoms selected in each of the sub-operations (c-1) and (c-2);

(c-5) obtaining a correlation coefficient according to said atomic distance obtained in the sub-operation (c-4), based on said upper and lower thresholds obtained in sub-operation (c-3);

(c-6) after completion of the sub-operation (c-5), returning to the sub-operation (c-2), selecting another unselected atom from said plurality of atoms included in said first molecule, executing the sub-operations (c-3) through (c-5) on said another atom selected in this operation, and updating said correlation coefficient; and (c-7) after completion of the sub-operation (c-6), returning to the sub-operation (c-0), selecting another unselected atom from said plurality of atoms in said second molecule, executing the sub-operations (c-2) through (c-6) on said another atom selected in this operation, and adding said correlation coefficient so as to obtain said similarity index; and (d) after completion of the operation (c), changing a relative position of said first molecule and second molecule in the three-dimensional coordinate system.

16. The molecular similarity evaluation program as set forth in claim 15, wherein said atomic distance obtained in the sub-operation (c-4) is a distance with respect to one of axes in Cartesian coordinate system.

17. The molecular similarity evaluation program as set forth in claim 15, wherein, in the operation (d), said relative position of said first and second molecules is changed in a direction to improve said similarity index.

18. The molecular similarity evaluation program as set forth in claim 13, wherein one of a van der Waals radius, atomic radius, and covalent radius of said atom can be a value specific to said atom.

19. The molecular similarity evaluation program as set forth in claim 13, wherein said upper threshold is obtained by multiplying a value specific to said atom by an upper limit constant.

20. The molecular similarity evaluation program as set forth in claim 13, wherein said lower threshold is obtained by multiplying a value specific to said atom by an lower limit constant.

21. The molecular similarity evaluation program as set forth in claim 19, wherein said upper limit constant is a value ranging from 1.0 to 1.3.

22. The molecular similarity evaluation program as set forth in claim 20, wherein said lower limit constant is a value ranging from 0.5 to 0.8.

* * * * *